(12) United States Patent
Vernon-Harcourt et al.

(10) Patent No.: US 9,878,074 B2
(45) Date of Patent: Jan. 30, 2018

(54) CANISTER STATUS DETERMINATION

(71) Applicant: Smith & Nephew PLC, London (GB)

(72) Inventors: Edward Vernon-Harcourt, Pulborough (GB); Jake Turner, Cambridge (GB); Benjamin Gordon, Cambridge (GB)

(73) Assignee: SMITH & NEPHEW PLC, London (GB)

( * ) Notice: Subject to any disclaimer, the term of this patent is extended or adjusted under 35 U.S.C. 154(b) by 738 days.

(21) Appl. No.: 14/454,181

(22) Filed: Aug. 7, 2014

(65) Prior Publication Data

US 2014/0352407 A1    Dec. 4, 2014

Related U.S. Application Data

(63) Continuation of application No. 12/672,468, filed as application No. PCT/GB2008/002346 on Jul. 9, 2008, now Pat. No. 8,843,327.

(30) Foreign Application Priority Data

Aug. 6, 2007 (GB) .................................. 0715259.8

(51) Int. Cl.
*A61M 1/00* (2006.01)

(52) U.S. Cl.
CPC ........ *A61M 1/0027* (2014.02); *A61M 1/0031* (2013.01); *A61M 1/0088* (2013.01); *A61M 2205/3331* (2013.01); *A61M 2205/3344* (2013.01); *A61M 2205/3382* (2013.01); *A61M 2209/02* (2013.01)

(58) Field of Classification Search
CPC .............. A61M 1/0027; A61M 1/0031; A61M 1/0088; A61M 2205/3331; A61M 2205/3344; A61M 2205/3382; A61M 2209/02
See application file for complete search history.

(56) References Cited

U.S. PATENT DOCUMENTS

| | | | |
|---|---|---|---|
| 4,708,010 | A | 11/1987 | Sgourakes |
| 4,936,832 | A | 6/1990 | Vaillancourt |
| 6,142,982 | A | 11/2000 | Hunt et al. |

(Continued)

FOREIGN PATENT DOCUMENTS

| | | |
|---|---|---|
| CA | 2349638 | 5/2000 |
| DE | 4016034 A1 | 11/1991 |

(Continued)

OTHER PUBLICATIONS

Canadian Office Action, re CA Application No. 2,695,409, dated Jun. 3, 2015.

(Continued)

*Primary Examiner* — Manuel L Barbee
(74) *Attorney, Agent, or Firm* — Knobbe, Martens, Olson & Bear LLP

(57) ABSTRACT

A method and apparatus are disclosed for determining status of a canister of a topical negative pressure (TNP) system. The method includes the steps of monitoring pressure provided by a pump element of the TNP system, determining at least one characteristic associated with the monitored pressure and determining status of at least one parameter associated with a canister of the TNP system responsive to the determined characteristics.

20 Claims, 10 Drawing Sheets

(56) References Cited

U.S. PATENT DOCUMENTS

| | | |
|---|---|---|
| 6,755,807 B2 | 6/2004 | Risk, Jr. et al. |
| 6,764,462 B2 | 7/2004 | Risk, Jr. et al. |
| 6,824,533 B2 | 11/2004 | Risk, Jr. et al. |
| 7,004,915 B2 | 2/2006 | Boynton et al. |
| 7,022,113 B2 | 4/2006 | Lockwood et al. |
| 7,092,797 B2 | 8/2006 | Gaines et al. |
| 7,438,705 B2 | 10/2008 | Karpowicz et al. |
| 7,553,306 B1 * | 6/2009 | Hunt ............ A61M 1/0031 604/304 |
| 7,811,269 B2 | 10/2010 | Boynton et al. |
| 7,927,319 B2 | 4/2011 | Lawhorn |
| 8,162,909 B2 | 4/2012 | Blott et al. |
| 8,298,200 B2 | 10/2012 | Vess et al. |
| 8,308,714 B2 | 11/2012 | Weston et al. |
| 8,444,392 B2 | 5/2013 | Turner et al. |
| 8,663,200 B2 | 3/2014 | Weston et al. |
| 8,771,259 B2 | 7/2014 | Karpowicz et al. |
| 8,814,842 B2 | 8/2014 | Coulthard et al. |
| 8,843,327 B2 | 9/2014 | Vernon-Harcourt et al. |
| 9,199,011 B2 | 12/2015 | Locke et al. |
| 9,314,557 B2 | 4/2016 | Ricci et al. |
| 9,421,309 B2 | 8/2016 | Robinson et al. |
| 2002/0198503 A1 | 12/2002 | Risk, Jr. et al. |
| 2003/0014022 A1 | 1/2003 | Lockwood et al. |
| 2003/0040687 A1 * | 2/2003 | Boynton ............ A61M 1/0031 601/6 |
| 2003/0097100 A1 | 5/2003 | Watson |
| 2005/0067191 A1 | 3/2005 | Miyamoto et al. |
| 2006/0129137 A1 | 6/2006 | Lockwood et al. |
| 2006/0198503 A1 | 9/2006 | Wahl et al. |
| 2007/0016152 A1 | 1/2007 | Karpowicz et al. |
| 2007/0032763 A1 | 2/2007 | Vogel |
| 2007/0118096 A1 | 5/2007 | Smith et al. |
| 2007/0179460 A1 | 8/2007 | Adahan |
| 2007/0219532 A1 | 9/2007 | Karpowicz et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2009/0012441 A1 * | 1/2009 | Mulligan ............ A61F 13/0203 602/57 |
| 2009/0299255 A1 | 12/2009 | Kazala, Jr. et al. |
| 2009/0306630 A1 * | 12/2009 | Locke ............ A61M 1/0001 604/543 |
| 2010/0125259 A1 | 5/2010 | Olson |
| 2010/0211030 A1 | 8/2010 | Turner et al. |
| 2010/0298792 A1 | 11/2010 | Weston et al. |
| 2010/0305490 A1 | 12/2010 | Coulthard et al. |
| 2011/0071483 A1 | 3/2011 | Gordon et al. |
| 2011/0077605 A1 | 3/2011 | Karpowicz |
| 2011/0236460 A1 | 9/2011 | Stopek et al. |
| 2012/0001762 A1 | 1/2012 | Turner et al. |
| 2012/0111963 A1 | 5/2012 | Gordon et al. |
| 2013/0150813 A1 | 1/2013 | Gordon et al. |
| 2013/0144227 A1 | 6/2013 | Locke et al. |
| 2014/0163493 A1 | 1/2014 | Weston et al. |
| 2015/0025482 A1 | 1/2015 | Begin et al. |

FOREIGN PATENT DOCUMENTS

| | | |
|---|---|---|
| DE | 102005014420 | 9/2006 |
| EP | 0777504 | 10/1998 |
| EP | 0853950 | 10/2002 |
| GB | 2235877 | 3/1991 |
| GB | 2307180 | 5/1997 |
| GB | 2342584 | 4/2000 |
| WO | WO 00/61206 | 10/2000 |
| WO | WO 03/030966 | 4/2003 |
| WO | WO 03/101508 | 12/2003 |
| WO | WO 2006/052745 | 5/2006 |
| WO | WO 2006/105892 | 10/2006 |
| WO | WO 2006/135934 | 12/2006 |
| WO | WO 2007/019038 | 2/2007 |
| WO | WO 2007/030599 | 3/2007 |
| WO | WO 2007/133618 | 11/2007 |
| WO | WO 2008/030872 | 3/2008 |
| WO | WO 2008/036360 | 3/2008 |
| WO | WO 2008/039314 | 4/2008 |
| WO | WO 2008/048481 | 4/2008 |
| WO | WO 2008/049029 | 4/2008 |
| WO | WO 2009/019419 | 2/2009 |
| WO | WO 2009/019495 | 2/2009 |
| WO | WO 2009/019496 | 2/2009 |
| WO | WO 2009/077722 | 6/2009 |
| WO | WO 2009/089390 | 7/2009 |
| WO | WO 2006/100053 | 5/2010 |

OTHER PUBLICATIONS

European Office Action, re EP Application No. 15183456.1, dated Dec. 23, 2015.

International Invitation to Pay, and Partial Search Report, re PCT Application No. PCT/US2014/050233, dated Nov. 5, 2014.

International Search Report and Written Opinion, re PCT Application No. PCT/US2014/050233, dated Jan. 7, 2015.

U.S. Appl. No. 14/210,062, filed Mar. 13, 2014, Miles et al.

Info V.A.C. User Manual—KCI—Dec. 2006 (76 pages).

International Preliminary Report on Patentability dated Feb. 9, 2010 for PCT/GB2008/002346 in 9 pages.

International Search Report from PCT/GB2008/002346 dated Oct. 27, 2008 in 7 pages.

International Search Report from PCT/GB2008/050515 dated Apr. 6, 2009 in 8 pages.

International Search Report from PCT/GB2008/050511 dated Oct. 10, 2008 in 5 pages.

International Search Report from PCT/GB2008/050507 dated Oct. 15, 2008 in 6 pages.

Canadian Office Action, re CA Application No. 2,695,409, dated Apr. 28, 2016.

Sadasivan, N. et al., "Studies on Frequency and Magnitude of Fluctuations of Pressure Drop in Gas-Solid Fluidised Beds", Power Technology, vol. 26, May-Jun. 1980, in 8 pages.

\* cited by examiner

CANISTER STATUS DETERMINATION

CROSS-REFERENCE TO RELATED APPLICATIONS

This application is a continuation of U.S. patent application Ser. No. 12/672,468, filed on Feb. 5, 2010, which is a U.S. National Phase of the PCT International Application No. PCT/GB2008/002346, filed on Jul. 9, 2008, which claims priority to Great Britain Patent Application No. 0715259.8, filed on Aug. 6, 2007. The disclosure of these prior applications is incorporated by reference in its entirety and should be considered a part of this specification.

BACKGROUND

Technical Field

The present invention relates to apparatus and a method for the application of topical negative pressure (TNP) therapy to wounds. In particular, but not exclusively, the present invention relates to a method and apparatus for determining status such as a fullness associated with a canister in a TNP system.

Description of the Related Art

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness. It will however be appreciated that from time to time errors may occur during operation of the TNP therapy unit. One particular problem which can occur is that when a canister utilised to filter and store waste product becomes full correct operation of the TNP system can be impeded. With current devices two pressure sensors are required on each side of a canister to detect such an event. A change in measured pressure between the two sensors implies a blocked canister filter which further implies a full canister. It will be appreciated that the use of two such sensors is both expensive and prone to error and requires complex processing elements to determine when a canister is full.

SUMMARY

It is an aim of the present invention to at least partly mitigate the above-mentioned problems.

It is an aim of embodiments of the present invention to provide a method and apparatus of determining status of a canister of a TNP system. More particularly, but not exclusively, it is an aim of embodiments of the present invention to provide a method and apparatus for determining when a canister of a TNP system is full.

It is an aim of embodiments of the present invention to provide an indication of when a canister of a TNP system is full without a requirement for two pressure sensors in the TNP system.

According to a first aspect of the present invention there is provided a method of determining status in a canister of a topical negative pressure (TNP) system, comprising the steps of:
 monitoring pressure provided by a pump element of the TNP system;
 determining at least one characteristic associated with the monitored pressure; and
 determining status of at least one parameter associated with a canister of the TNP system responsive to the determined characteristics.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a foam or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of upto −75 mmHg, upto −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus from the carry case.

The carry case may be provided with an aperture covered by a displaceable flap to enable user access to a keypad for varying the therapy applied by the apparatus.

According to a second aspect of the present invention, there is provided apparatus for determining status in a canister of a topical negative pressure (TNP) system, comprising:
 a canister arranged to collect exudate from an aspirant tube locatable at a wound site;
 a pump element arranged to pump air and/or exudate from the tube through the canister;
 a pressure sensor for monitoring pressure provided by the pump element; and
 a processing unit comprising at least one processing element that determines at least one characteristic associated with the monitored pressure and determines status of at least one parameter associated with the canister responsive to the determined characteristic.

According to a third aspect of the present invention there is provided a method of determining the occurrence of a blockage of a canister filter in a topical negative pressure (TNP) system comprising the steps of:
 monitoring pressure provided by a pump element of the TNP system; and
 determining if a monitored pressure falls below a pre-determined threshold value.

According to a fourth aspect of the present invention there is provided apparatus for determining the occurrence of a blockage of a canister filter in a topical negative pressure (TNP) system, comprising:
 a canister arranged to collect exudate from an aspirant tube locatable at a wound site;
 a filter arranged to filter air in the canister;
 a pump element arranged to pump air and/or exudate from the tube through the canister;
 a pressure sensor arranged to monitor pressure generated by the pump; and
 a processing unit comprising at least one processing element arranged to determine if a monitored pressure falls below a pre-determined threshold value.

Embodiments of the present invention provide a method and apparatus which allows the status of a canister of a topical negative pressure (TNP) system to be determined without the necessity to provide two pressure sensors in the TNP system. By monitoring the magnitude of pressure 'pulses' created by a pump possible leakage or the fact that a canister filter may be full can be detected. Optionally two or more sensors can be used if very prompt detection of errors is desired.

BRIEF DESCRIPTION OF THE DRAWINGS

In order that the present invention may be more fully understood, examples will now be described by way of illustration only with reference to the accompanying drawings, of which.

DETAILED DESCRIPTION

Figure 1:
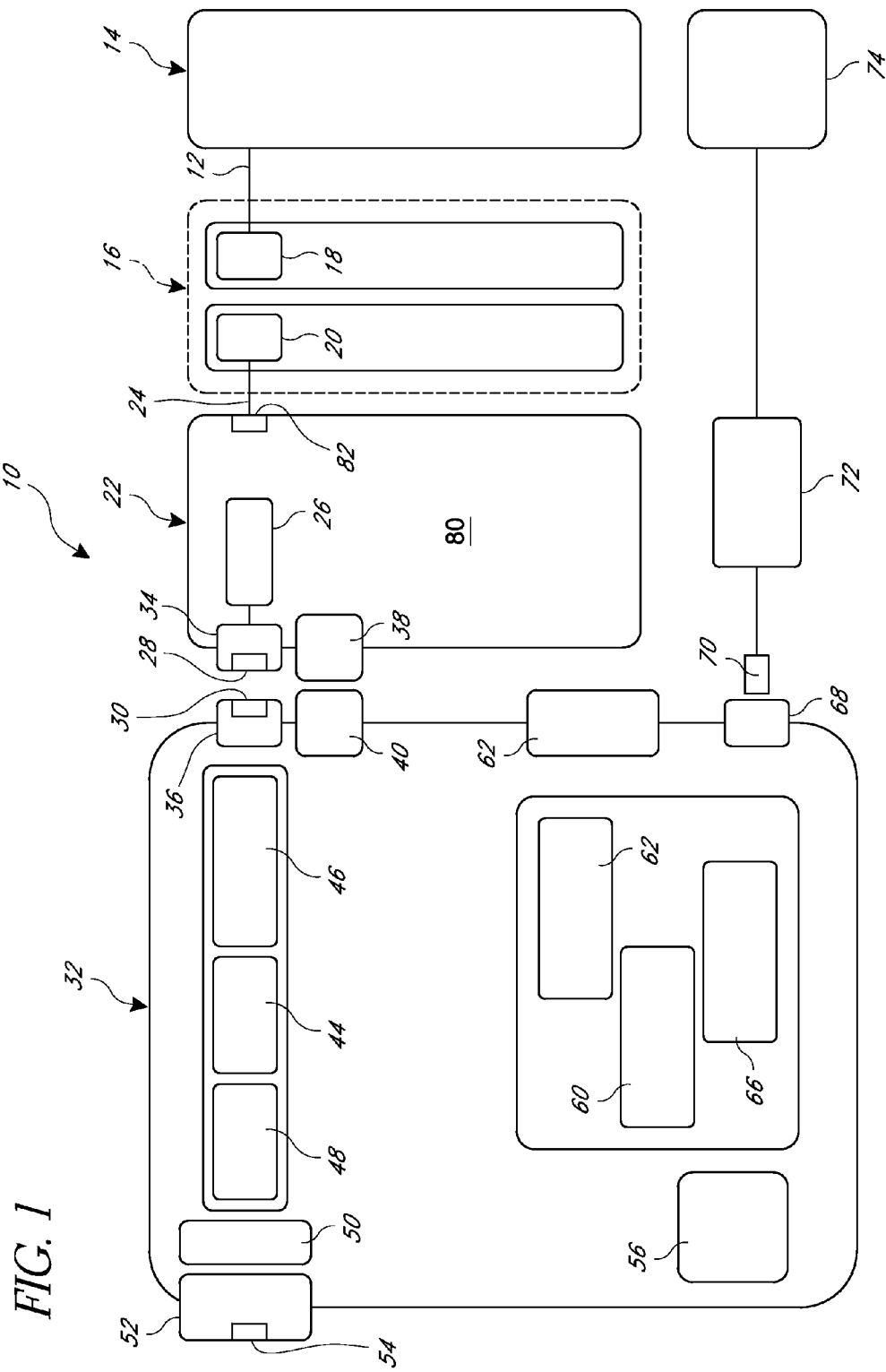
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
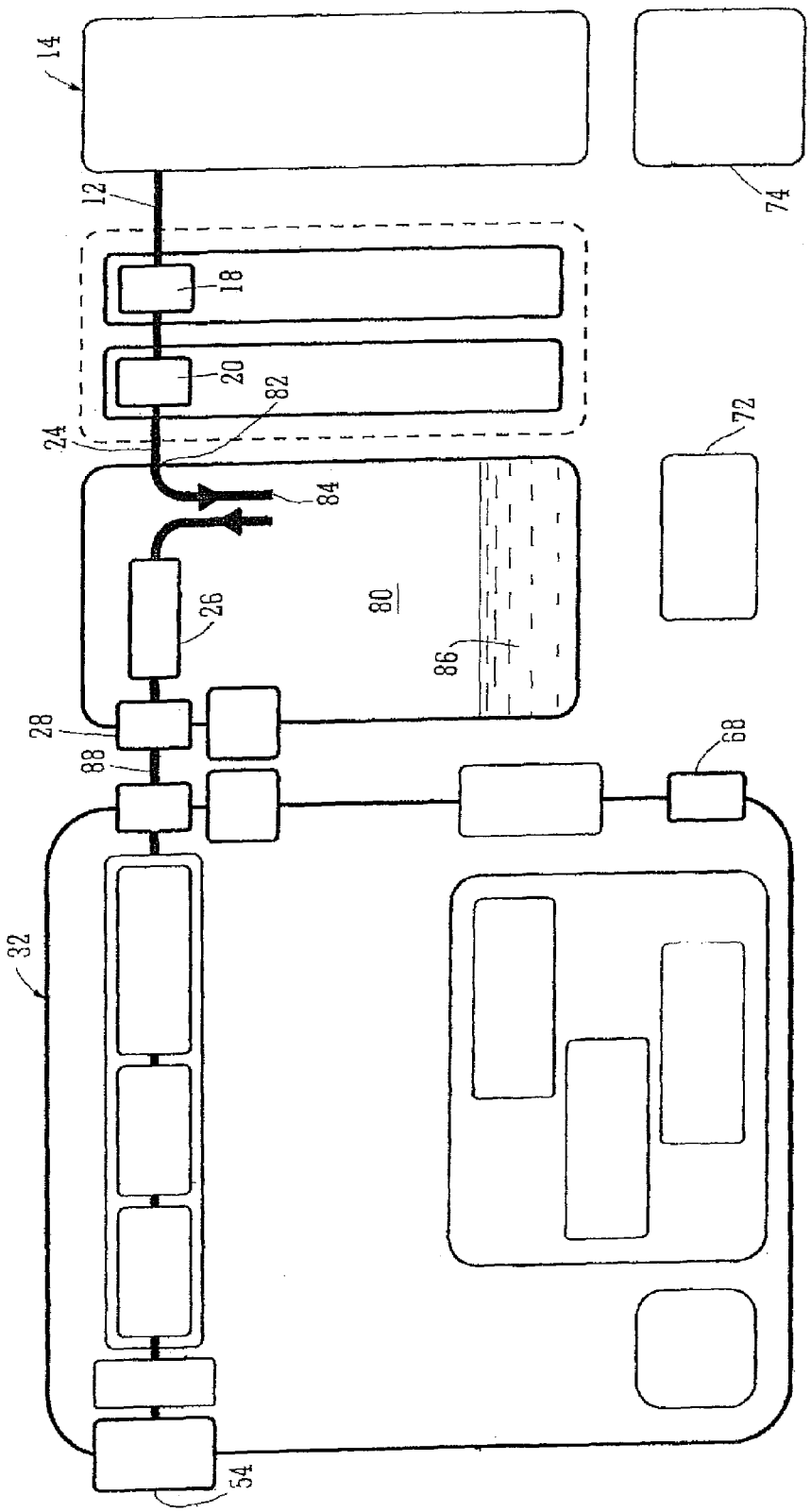
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
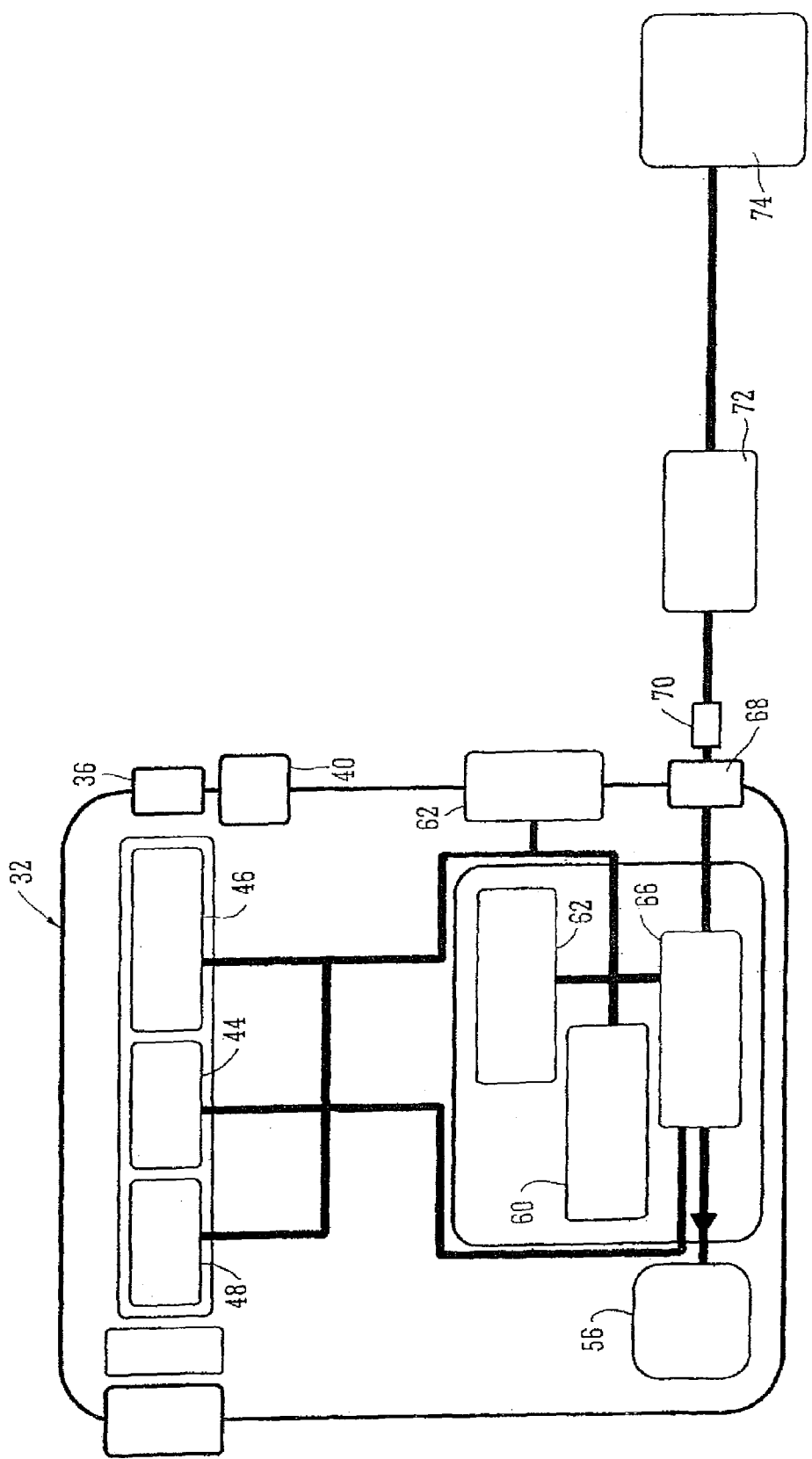
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
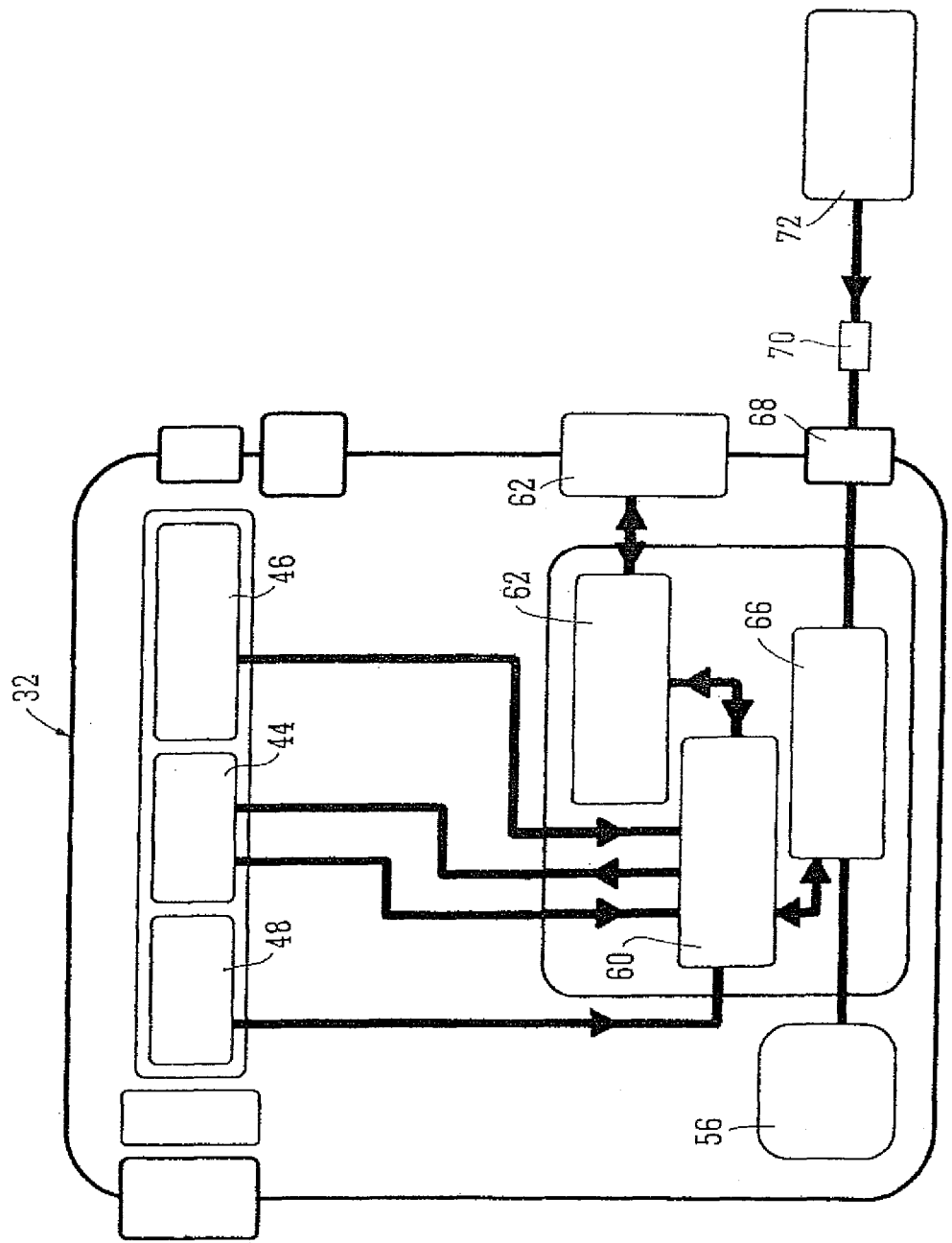
FIG. 4 shows a similar generalised schematic block diagram to FIG. 3 of the device unit and showing control system data paths for controlling the various functions and components of the apparatus.
Figure 5:
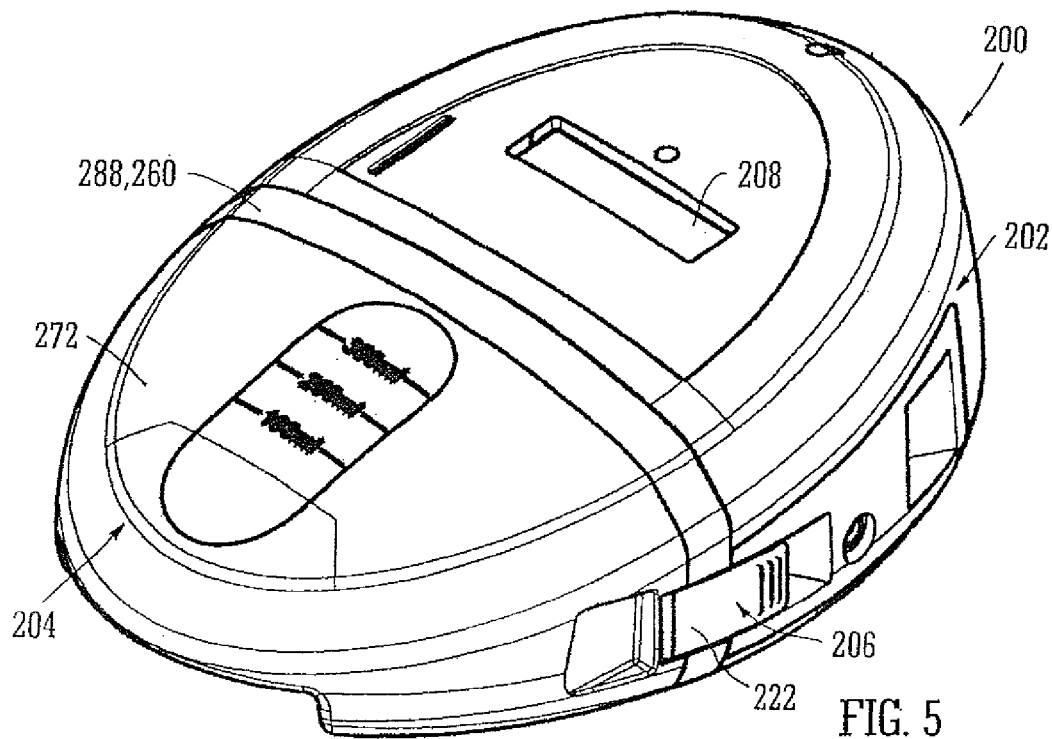
FIG. 5 shows a perspective view of an apparatus.
Figure 6:
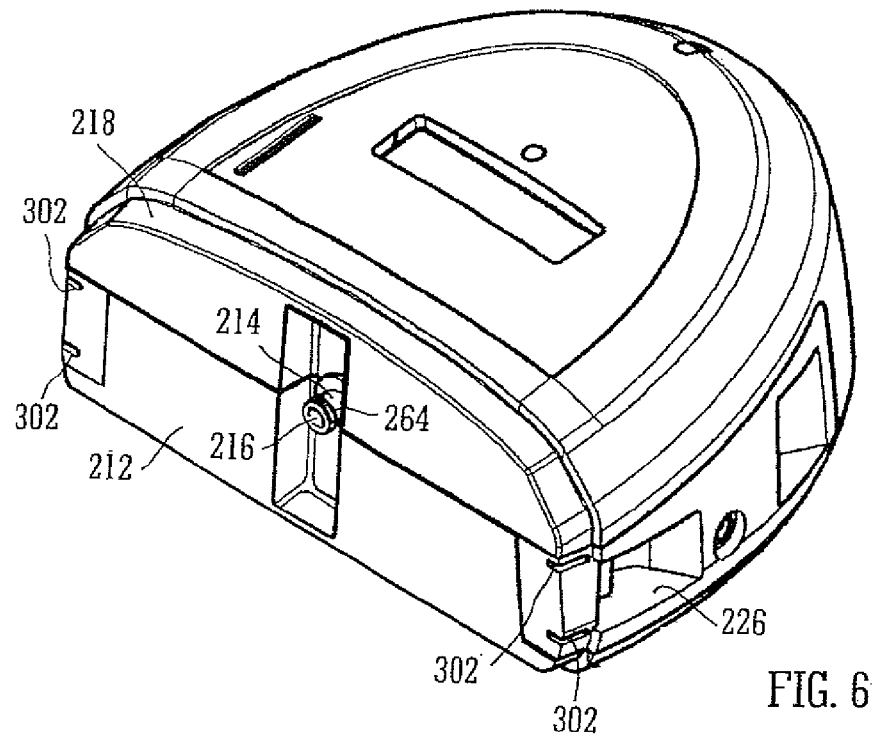
FIG. 6 shows a perspective view of an assembled device unit of the apparatus of FIG. 5.
Figure 7:
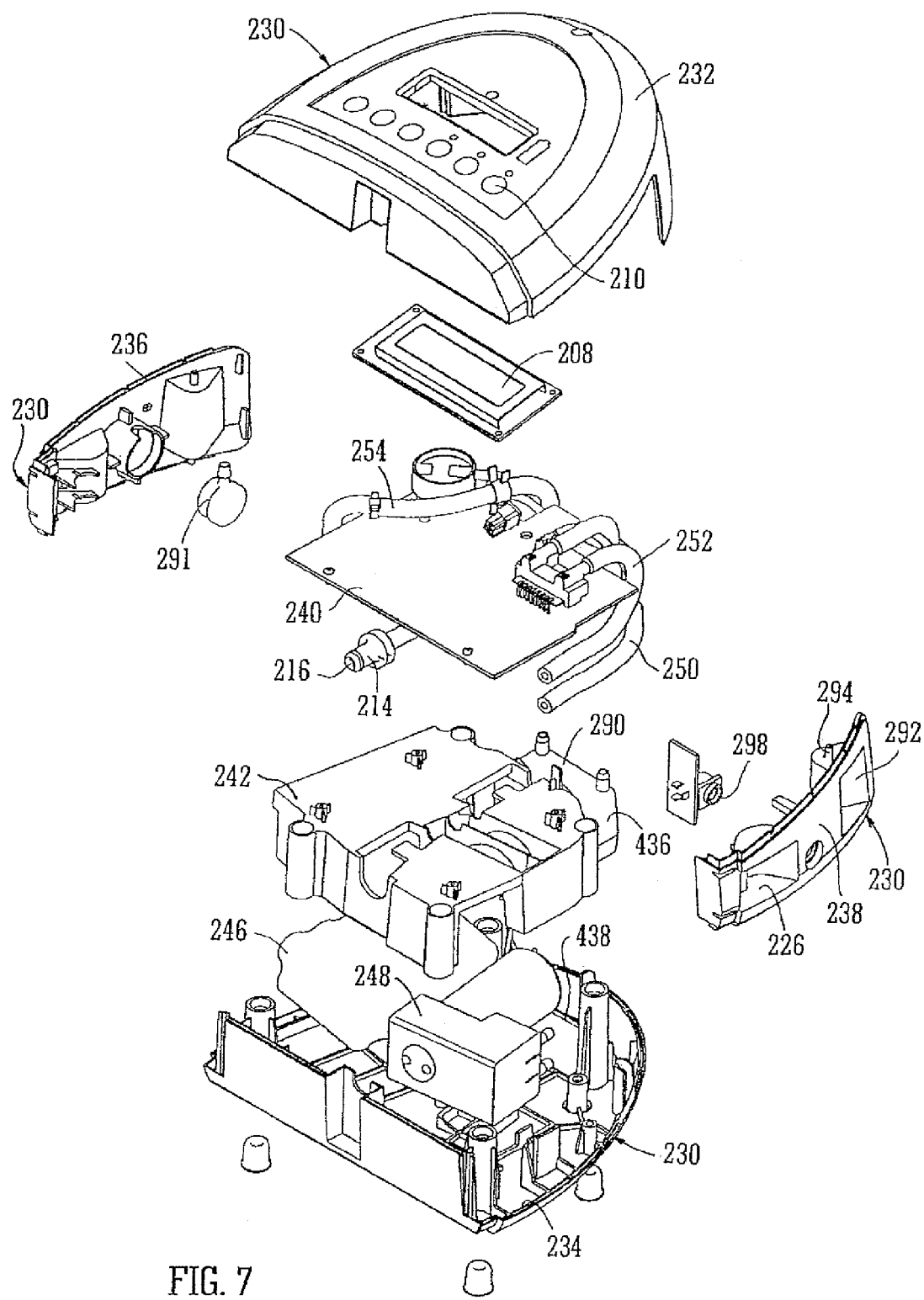
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
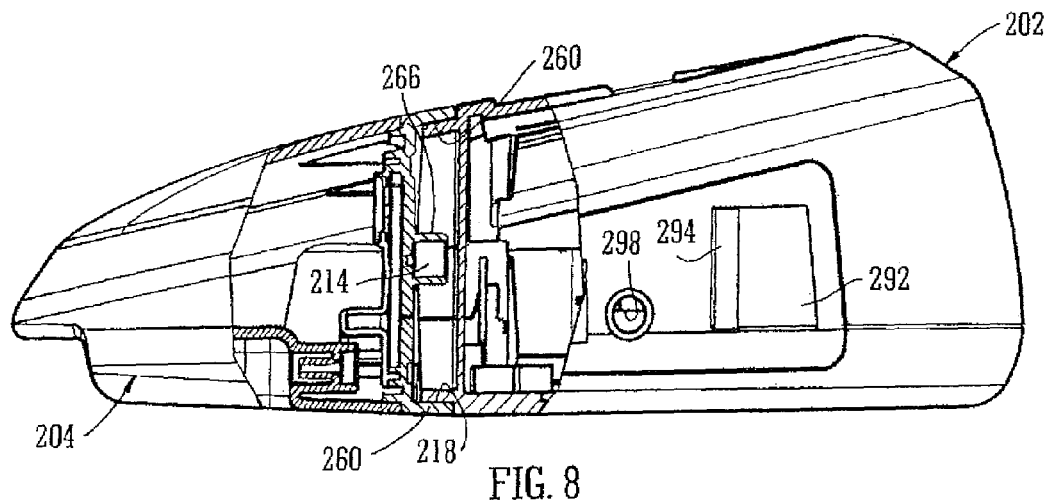
FIG. 8 shows a partially sectioned side elevation view through the interface between a waste canister and device unit of the apparatus.
Figure 9:
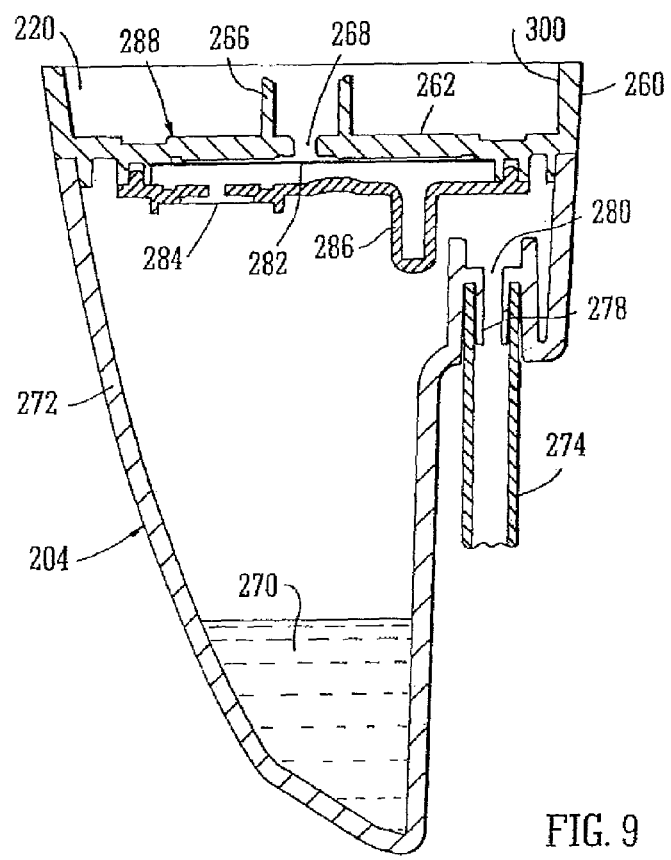
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. These views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
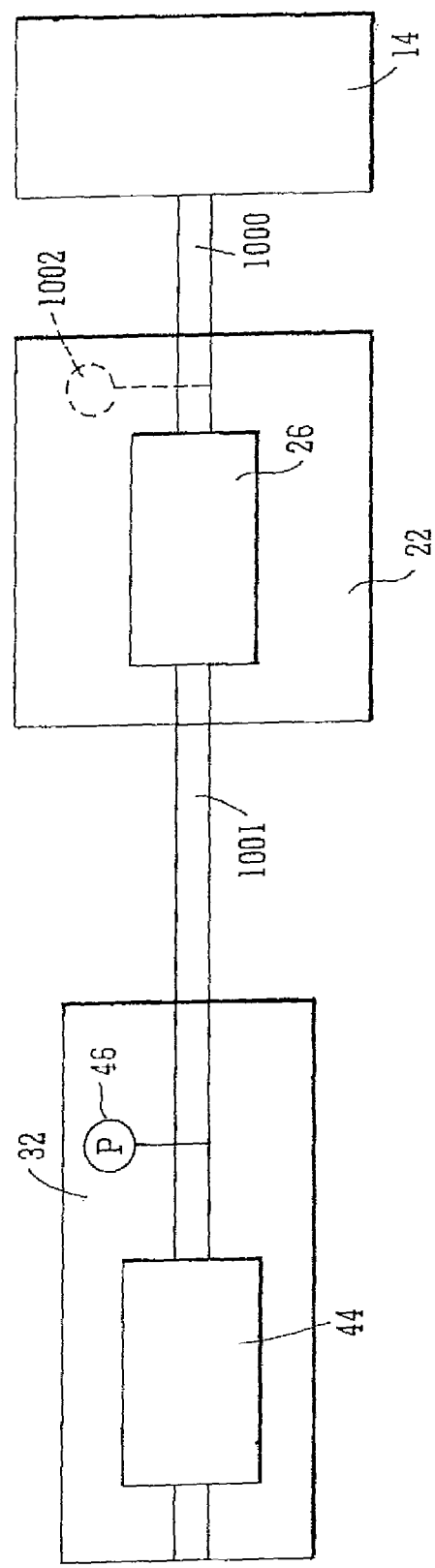
FIG. 10 illustrates part of a TNP system.

FIG. 10 illustrates schematically a TNP system. A more thorough discussion of many of the parts shown have been made previously with respect to FIG. 1. It is to be noted that a connecting tube 1000 is illustrated as connecting the dressing 14 to the canister 22 whilst a further connecting tube 1001 is illustrated connecting the canister to the aspirant system 32. These tubes are shown for illustrative purposes and it will be appreciated that rather than the tubes connector portions 34, 36 can be utilised between the aspirant system and canister and that likewise an inline connector 16 may be connected between the dressing and canister.

An aspirant pump 44 used to create the negative pressure of the TNP system is a diaphragm pump. This is utilised to move air and create the vacuum in the wound bed. The diaphragm acts as a miniature piston and, hence creates small pulses of pressure as it moves backwards and forwards. These pulses interfere with the flow of air through the system and their magnitude as measured, for example at the pump inlet, varies according to the status of the canister. This relationship is illustrated more clearly in FIG. 11. It will be appreciated that other types of pump providing a pulsatile output can be used according to other embodiments of the present invention.

Figure 11:
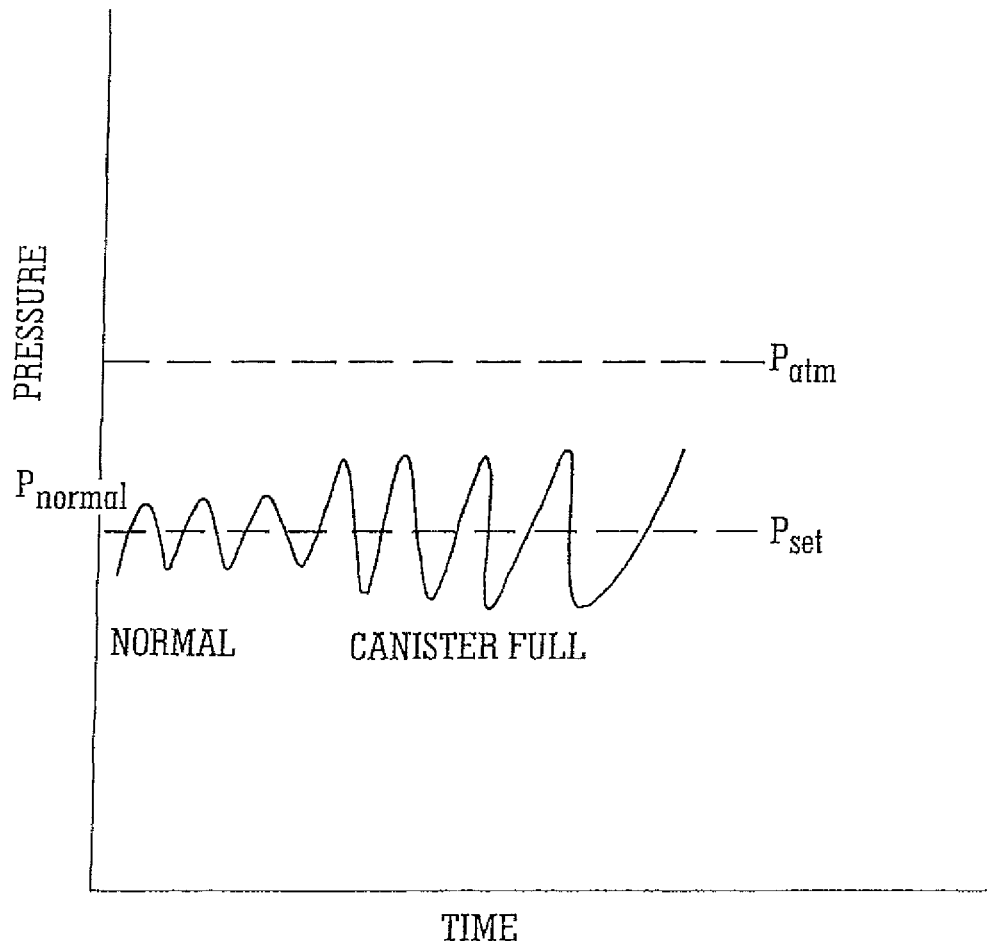
FIG. 11 illustrates how magnitude and/or frequency of pulses can vary.

As shown in FIG. 11 during a normal mode of operation the pressure pulses have relatively small magnitude centred around a pre-set pressure $P_{set}$. A maximum value of these pressure pulse readings $P_{normal}$ can thus be utilised to determine when a pump is working efficiently.

Thus by measuring the magnitude of the pressure pulses it is possible to detect whether a canister is blocked. FIG. 11 also illustrates operation with a canister filter full. Whilst the negative pressure delivered by the pump remains less than atmospheric pressure $P_{atm}$ the magnitude of the pulses is shown as later increased substantially above the predetermined normal operating pressure $P_{normal}$. It will also be appreciated that minimum pressure values taken at the minimum of the pressure curve or some other common sampling point could be utilised and compared as a predetermined set value. FIG. 11 thus illustrates how during a normal mode of operation the flow path provided by the tubing 1000, canister 22, tubing 1000 and tubing in the aspirant system provides a sufficiently large volume so that pulsatile elements of pressure variation caused by the diaphragm of the pump are moderated but still are detectable. When a canister filter 26 becomes full the flow path volume 'seen' by the aspirant pump is much diminished and includes the volume only of the tubing 1001 and tubing elements in the aspiration system. As such the pulsatile elements associated with the pumping pressure are 'magnified'.

It will also be appreciated that the frequency of pumping may also vary when a canister filter becomes full. The frequency can thus likewise additionally or optionally be utilised to determine status of at least one parameter such as fullness or leakiness associated with a canister of a TNP system.

Rather than initiating an alarm when the canister filter is full, the magnitude or frequency characteristics of the pressure can also be continually or periodically monitored with a magnitude being used to indicate current status. This can continually provide an indication such as percentage fullness which may be displayed via a user interface.

It will be appreciated that aptly the pressure is measured close to the location where the aspirant pump is provided in a TNP system. This is because damping effects caused by the volume of air in the flow path are minimised close to the pump inlet.

Figure 12:
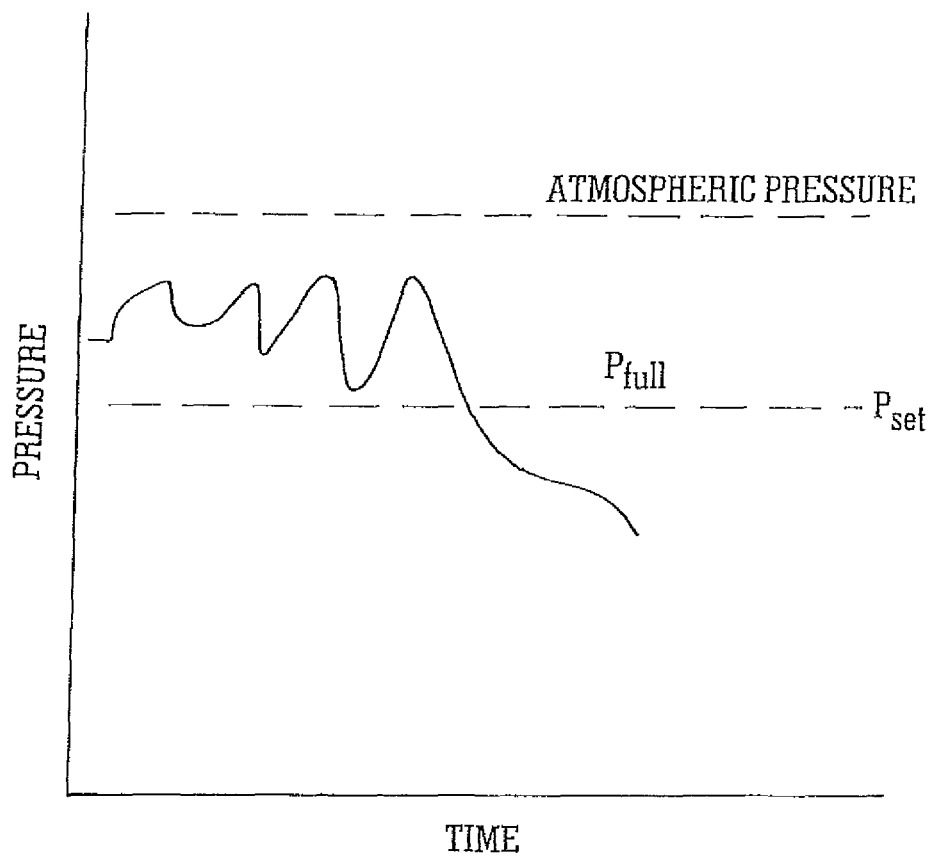
FIG. 12 illustrates pressure with a blocked canister filter.

FIG. 12 illustrates how embodiments of the present invention can utilise an optional pressure sensor 1002 to monitor pressure at a location downstream of a canister filter 26 between the filter and dressing 14. As illustrated in FIG. 12 due to the substantial volume of the flow path during normal operation at the pressure sensor 1002 the pulsatile effects on pressure are muffled somewhat. However as a canister filter fills this results in a blockage in the flow path. The sensor 1002 thus no longer measures any pulse like flow from the pump. When this measured pressure falls below a predetermined threshold value $P_{SET}$ an alarm in the form of an audible and/or visual cue can be initiated.

Embodiments of the present invention thus provide a manner in which the status of a canister such as a fullness of a filter associated with a canister can be determined by monitoring pressure provided by a pump of a TNP system. By determining a characteristic such as magnitude or frequency associated with the monitored pressure the status of at least one parameter such as fullness or a leak in a flow path associated with a canister can be determined. This can be achieved with only a single pressure sensor which obviates the need associated with prior known devices for two pressure sensors.

Embodiments of the present invention utilise a single pressure sensor downstream of a canister filter between a canister filter and a dressing of a TNP system to determine when a canister filter is full and needs replacing.

Embodiments of the present invention make use of two pressure sensors. One pressure sensor is located proximate to a pump inlet whilst a further pressure sensor is located downstream of a canister filter. This enable prompt detection of a leak and/or full canister filter.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A method of operating a topical negative pressure (TNP) system comprising a negative pressure source, a pressure sensor, a canister, and a controller, the method comprising:
aspirating, by the negative pressure source, fluid from a wound;
collecting, by the canister, at least some fluid removed from the wound;
monitoring, by the pressure sensor, pressure pulses generated by the negative pressure source;
comparing, by the controller, a magnitude of the pressure pulses to a magnitude threshold, wherein the magnitude of the pressure pulses increases as a level of fluid in the canister increases;
by the controller, determining, before a canister filter associated with the canister becomes blocked, that the level of fluid in the canister is above a canister empty level and below a canister full level based on the comparison of the magnitude of the pressure pulses to the magnitude threshold; and
outputting, by the controller, to a user interface an indication for presentation to a user, the indication denoting that the level of fluid in the canister is above the canister empty level and below the canister full level.

2. The method of claim 1, further comprising:
comparing a frequency of the pressure pulses to a frequency threshold; and
determining the level of fluid in the canister based on the comparison of the frequency of the pressure pulses to the frequency threshold.

3. The method of claim 2, wherein said comparing the frequency of the pressure pulses comprises comparing the frequency of the pressure pulses to the frequency threshold over a period of time.

4. The method of claim 1, wherein said comparing comprises comparing the magnitude of the pressure pulses to the magnitude threshold over a period of time.

5. The method of claim 1, wherein said monitoring comprises monitoring the pressure pulses at an inlet of the negative pressure source.

6. The method of claim 1, further comprising:
comparing, by the controller, the magnitude of the pressure pulses to another magnitude threshold;
by the controller, determining that the level of fluid in the canister is at the canister full level based on the comparison of the magnitude of the pressure pulses to the another magnitude threshold; and
outputting, by the controller, to the user interface another indication for presentation to the user, the another indication denoting that the level of fluid in the canister is at the canister full level.

7. The method of claim 1, wherein that the level of fluid in the canister is above the canister empty level and below the canister full level is determined using pressure data from no pressure sensor other than the pressure sensor.

8. The method of claim 1, further comprising audibly presenting the indication with the user interface to the user.

9. The method of claim 1, further comprising visually presenting the indication with the user interface to the user.

10. A topical negative pressure (TNP) apparatus comprising:
a negative pressure source configured to aspirate fluid from a wound;
a canister configured to collect at least some fluid removed from the wound;
a canister filter associated with the canister;
a pressure sensor configured to monitor pressure pulses generated by the negative pressure source; and
a controller configured to:
compare a magnitude of the pressure pulses to a magnitude threshold, wherein the magnitude of the pressure pulses increases as a level of fluid in the canister increases; and
determine, before the canister filter becomes blocked, whether the level of fluid in the canister is above a canister empty level and below a canister full level based on the comparison of the magnitude of the pressure pulses to the magnitude threshold.

11. The TNP apparatus of claim 10, wherein the controller is further configured to:
compare a frequency of the pressure pulses to a frequency threshold; and
determine the level of fluid in the canister based on the comparison of the frequency of the pressure pulses to the frequency threshold.

12. The TNP apparatus of claim 11, wherein the controller is configured to compare the frequency of the pressure pulses to the frequency threshold over a period of time.

13. The TNP apparatus of claim 10, wherein the controller is configured to compare the magnitude of the pressure pulses to the magnitude threshold over a period of time.

14. The TNP apparatus of claim 10, wherein the pressure sensor is configured to monitor the pressure pulses at an inlet of the negative pressure source.

15. The TNP apparatus of claim 10, further comprising a user interface configured to indicate that the level of fluid in the canister is above the canister empty level and below the canister full level.

16. The TNP apparatus of claim 15, wherein the user interface is configured to audibly indicate that the level of fluid in the canister is above the canister empty level and below the canister full level.

17. The TNP apparatus of claim 15, wherein the user interface is configured to visually indicate that the level of fluid in the canister is above the canister empty level and below the canister full level.

18. The TNP apparatus of claim 15, wherein the user interface is configured to indicate with a percentage fullness indicator that the level of fluid in the canister is above the canister empty level and below the canister full level.

19. The TNP apparatus of claim 10, wherein the controller is further configured to:
compare the magnitude of the pressure pulses to another magnitude threshold; and
determine whether the level of fluid in the canister is at the canister full level based on the comparison of the magnitude of the pressure pulses to the another magnitude threshold.

20. The TNP apparatus of claim 10, wherein the controller is configured to determine, before the canister filter becomes blocked, whether the level of fluid in the canister is above the canister empty level and below the canister full level with pressure data from no pressure sensor other than the pressure sensor.

* * * * *